United States Patent
Hjorth

(10) Patent No.: US 6,626,882 B2
(45) Date of Patent: Sep. 30, 2003

(54) ABSORBENT ARTICLE

(75) Inventor: Madeleine Hjorth, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/950,669

(22) Filed: Sep. 13, 2001

(65) Prior Publication Data

US 2002/0032425 A1 Mar. 14, 2002

Related U.S. Application Data

(60) Provisional application No. 60/230,928, filed on Sep. 13, 2000.

(51) Int. Cl.[7] .......................... A61F 13/15; A61F 13/20; G09B 25/00
(52) U.S. Cl. .................. 604/392; 604/385.01; 434/395
(58) Field of Search ........................... 604/385.01, 386, 604/389–396; 434/260, 395; 24/33 L; 2/246, 279

(56) References Cited

U.S. PATENT DOCUMENTS

| | | | | |
|---|---|---|---|---|
| 3,638,651 A | * | 2/1972 | Torr ........................... | 604/390 |
| 4,662,875 A | * | 5/1987 | Hirotsu et al. ............... | 604/389 |
| 5,133,707 A | * | 7/1992 | Rogers et al. ............... | 604/389 |
| 5,695,488 A | * | 12/1997 | Sosalla ........................ | 604/392 |
| 5,776,123 A | * | 7/1998 | Goerg et al. ............ | 604/385.01 |
| 6,045,543 A | * | 4/2000 | Pozniak et al. ......... | 604/385.01 |
| 6,287,287 B1 | * | 9/2001 | Elsberg ................. | 604/385.03 |
| 6,322,552 B1 | * | 11/2001 | Blenke et al. .............. | 604/540 |
| 2002/0062117 A1 | * | 5/2002 | Raufman et al. ........... | 604/389 |
| 2002/0091369 A1 | * | 7/2002 | Hansson ...................... | 604/392 |

FOREIGN PATENT DOCUMENTS

| | | |
|---|---|---|
| EP | 287388 | 10/1988 |
| EP | 409307 | 1/1991 |
| EP | 528282 | 2/1993 |
| EP | 605012 | 7/1994 |
| EP | 0605014 | 7/1994 |
| FR | 2586558 | 3/1987 |
| GB | 2135568 | * 9/1984 |
| JP | 11332910 | 12/1997 |
| WO | 91/08725 | 6/1991 |
| WO | 95/19753 | 7/1995 |

* cited by examiner

*Primary Examiner*—Karin Reichle
(74) *Attorney, Agent, or Firm*—Burns, Doane, Swecker & Mathis, L.L.P.

(57) ABSTRACT

An absorbent article includes a pair of belt portions (9, 10) attached to the rear portion (6), alternatively the front portion (5), of the article and intended to be fastened together around the waist of the wearer, wherein one belt portion (9) at its end carries a fastener (11) intended to be attached against the opposite belt portion (10) and where in the front portion (5), alternatively the rear portion (6), is provided with fasteners (8), intended to be attached to the belt portions (9, 10), in such a way that the article will assume a pant shape, with the belt portions (9, 10) forming a part of the waist portion of the pant. The belt portions (9, 10) are provided with at least one element for identification and distinction of the different ends of the belt portions (9*a*, 10*a*) from each other.

4 Claims, 2 Drawing Sheets

ABSORBENT ARTICLE

CROSS REFERENCE TO RELATED APPLICATIONS

The present application claims the benefit of U.S. Provisional Application, Serial No. 60/230,928, filed in the United States on Sep. 13, 2000.

TECHNICAL FIELD

The present invention refers to an absorbent article such as a diaper or an incontinence guard comprising a liquid permeable topsheet, a liquid impermeable backsheet and an absorbent body enclosed therebetween, said article having a front portion, a rear portion and a crotch portion therebetween, and further is provided with a pair of belt portions attached to the rear portion, alternatively the front portion of the article, which are intended to be fastened together around the waist of the wearer and where said front portion, alternatively the rear portion, is provided with attachment means intended to be attached to the belt portions, in such a way that the article will assume a pant-like shape, in which the belt portions form a part of the waist portion of the pant.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is further known, through, e.g., EP-A-0 287 388, EP-A-0 409 307, EP-A-0 528 282, EP-A-0 605 012 and FR-A-2 586 558, to attach the front and rear portions of the article by means of a belt, in which the possibilities to adjust the fit are improved. The belt further provides a simplified change of diaper or incontinence guard, especially when the patient is standing up.

On a common type of belt diaper the belt portions are first attached around the waist on the patient and then the front portion of the diaper is attached to the outside of the belt using fastening means such as hook and loop fasteners, tape tabs, etc., arranged at front portion and/or the belt. Usually the hook material of the hook and loop fasteners or the tape tabs are arranged on the front portion, whilst the outside portions of the belt function as reception surface for these means. The belt portions are folded together with the rest of the product as a package before usage. One problem is that for elderly people or persons having a weak sight capability or when there are bad light conditions, it may be difficult to identify the different parts of the diaper and to understand how the diaper is to be applied on the body with a folded belted product. In hospitals, in elderly care or the like, the products usually are being stored without wrapping material. Thus, there is no easily available instruction showing the user how to apply the product. It would therefore be desirable to be able to provide a diaper or incontinence guard which more intuitively and in a self-instructing way shows how to apply the product.

SUMMARY OF THE INVENTION

An object of the present invention is to provide a diaper or incontinence guard which guides the user in how to apply the product. This object is solved by providing an absorbent article comprising a liquid permeable topsheet, a liquid impermeable backsheet and an absorbent body enclosed therebetween, said article further having a front portion, a rear portion and a crotch portion therebetween, and a pair of belt portions attached to one of the rear portion and the front portion of the article which are adapted to be fastened together around a waist of a wearer, wherein one of the belt portions has a free end which carries a fastener adapted to be attached against the other belt portion and wherein the other of the front and rear portion includes fasteners adapted to attach the other of the front portion and rear portion to the belt portions in such a way that the article will assume a pant shape, where the belt portions form a part of the waist portion of the pant, and wherein the free end for the one of said belt portions is distinct and can be readily distinguished from the free end of the other belt portion by a person with weak eyesight or in bad light conditions.

BRIEF DESCRIPTION OF DRAWINGS

The embodiments of the invention will be described in more detail below with reference to the embodiments shown in the accompanying drawings.

DESCRIPTION OF AN EMBODIMENT

Figure 1:
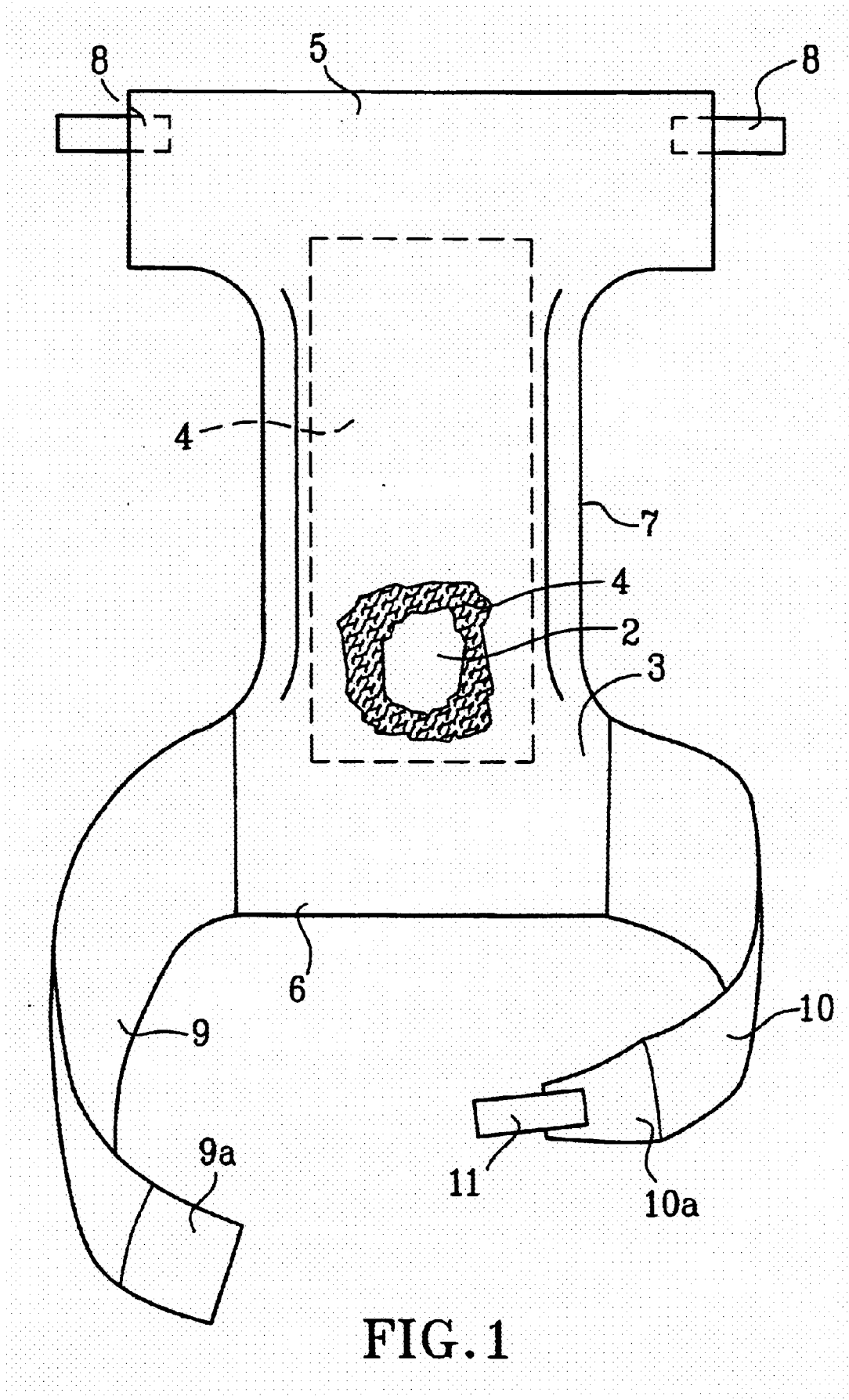
FIG. 1 shows schematically a perspective view of a diaper or incontinence guard according to an embodiment of the invention, partly in cutaway.

FIG. 1 shows an embodiment of a diaper or incontinence guard 1 comprising a liquid impermeable backsheet 2, a liquid permeable topsheet 3 and an absorbent body 4 enclosed therebetween. The liquid permeable topsheet 3 can include a nonwoven material, e.g., a spunbond material of continuous filaments, a meltblown material, a bonded carded fibrous web or a perforated plastic film. The liquid impermeable backsheet 2 may include a plastic film, a nonwoven material coated with a liquid impervious material or a hydrophobic nonwoven material which resists liquid penetration.

The topsheet 3 and the backsheet material 2 have a somewhat greater extension in the plane than the absorbent body 4 and extend outside the edges thereof. The layers 2 and 3 are connected to each other within the projecting portions thereof, e.g., by gluing or welding by heat or ultrasound.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well known to the person skilled in the art and does therefore not have to be described in detail. The thin absorbent bodies which are common in for example, baby diapers and incontinence guards often comprise a compressed mixed or layered structure of cellulosic fluff pulp and superabsorbent.

The diaper/incontinence guard is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 exhibits a pair of tape tabs 8 or another type of fastening means such as hook and loop fasteners.

A pair of belt portions 9 and 10 are attached at one end, e.g., glued or ultrasonically welded, to the rear portion 6 of the diaper. The belt portions 9, 10 are, at their opposite ends, intended to be fastened together, e.g., by means of a tape tab 11 which is attached against the outside of the opposite belt portion. Instead of tape tabs any optional fastening means may be used such as hook and loop fasteners. The tape tabs 8 of the front portion 5 are intended to be attached against the outside portions of the belt portions 9, 10 in order to fasten together the diaper/incontinence guard in the desired pant-like shape.

The width of the belt portions 9 should be between 5–20 cm, preferably between 7–15 cm.

The belt portions 9, 10 are preferably a laminate of a carrier material, which forms the outside of the belt, and a soft nonwoven, which forms the inside of the belt intended to be in direct contact with the skin of the user. A suitable nonwoven material can be a spunbond material of, e.g., polypropylene or polyethylene fibres. Conjugate fibres may also be used. Another suitable nonwoven material can be a carded thermobonded material of, e.g., polypropylene, polyester or conjugate fibres. As carrier material, a plastic film or another suitable material, e.g., nonwoven, may be used. The carrier material should be adapted to function as a reception surface for both the attachment means 8 and 11. In those cases where other types of fastening means are used instead of tape tabs, e.g., hook and loop fasteners, another kind of carrier material may be appropriate, especially a nonwoven material. Also elastic laminates are suitable to use as material in the belt portions. The ends of the belt portions 9, 10 are denoted 9a and 10a, respectively.

When the belt diaper is to be used, it is unfolded from its folded state and the belt portions 9, 10 are unfolded. In order to, in a more intuitive and self-instructing way, guide the user how to use the belt diaper, is it important that the user easily, by using eyesight or sense, is able to determine where the ends are in order to more easily grasp them. Both ends of the belt portions should also be distinguished from each other, so as to determine which belt portion is to be applied on top of the other. This makes usage easier for persons having weaker eyesight or during application in bad light conditions. The ends of the belt portions are therefore designed with means to identify and to distinguish the different ends 9a, 10a of the belt portions 9, 10 from each other.

This means may include a geometric difference between the ends of the belt portions, whereby it is possible to, using the sense of touch in the finger tips as well as the sense of sight, identify where the ends of the belt portions 9a, 10a are, partly to more easily be able to grasp them and partly be able to distinguish them from each other. One end of a belt portion, usually the right one, carries fastening means 11 and is therefore intended to be applied on top of the end of an opposite belt portion, usually the left one. Analogously with an ordinary waist belt, where the end which is to be placed on the outside of the other one exhibits a tapering shape, one may design the end of a belt portion 10a carrying the fastening means 11 more narrow whilst the end of the opposite belt portion 9a is broader with a blunt end. The user will intuitively place the belt portions 9, 10 in a correct mode, i.e., with the part exhibiting the broader end 9a beneath.

Alternatively or as a complement to this geometric shape difference, the ends of the belt portions may be provided with distinguishing colors, partly to be able to distinguish the ends of the belt portions 9a, 10a from each other and partly to distinguish them from the rest of the belt portions in order to more easily be able to find the ends. This color may be conspicuous or even fluorescent in order to readily identify the ends of the belt portions 9a, 10a.

Figure 2A:
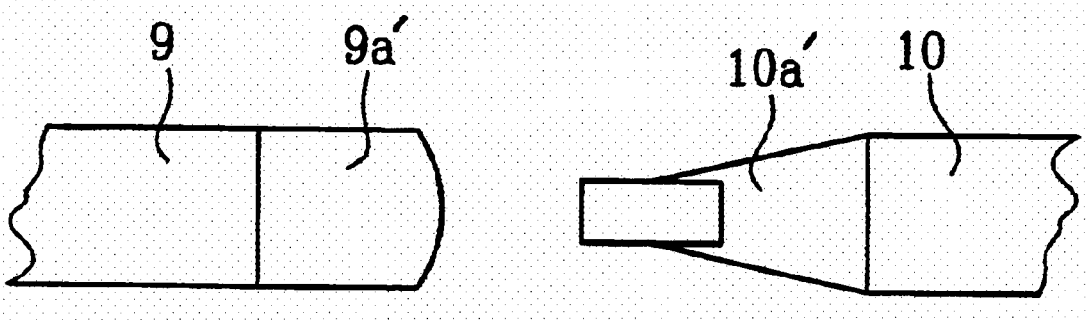
FIGS. 2a and 2b show additional examples of different belt ends on a diaper according to FIG. 1.
Figure 2B:
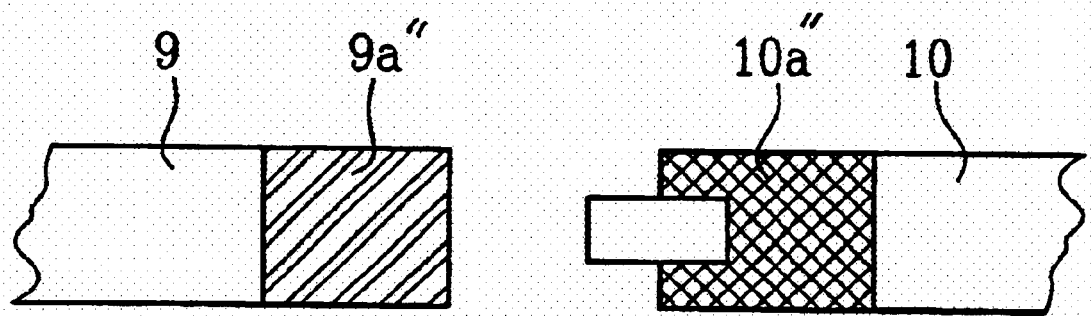

FIGS. 2a and 2b show additional examples of different belt ends, 9a', 10a' and 9a'', 10a'', which could be used on the diaper in FIG. 1.

The invention is of course not limited to the above described embodiment but can be modified within the scope of the claims.

What is claimed is:

1. An absorbent article comprising a liquid permeable topsheet, a liquid impermeable backsheet and an absorbent body enclosed therebetween, said article further having a front portion, a rear portion, a crotch portion between said front portion and said rear portion, and a pair of belt portions, attached to one of the rear portion and the front portion of the article, adapted to be fastened together around a waist of a wearer to form a belt having an exterior surface, wherein one of the belt portions has a free end which carries a fastener adapted to be attached to an exterior surface of the other of the belt portions and wherein the other of the front portion and the rear portion includes fasteners adapted to attach the other of the front portion and the rear portion to the exterior surface of the belt in such a way that the article assumes a pant shape with the belt portions forming a part of a waist portion of the pant, and wherein a color difference exists between the free end of the one of said belt portions and a free end of the other of the belt portions and a color difference exists between the ends free and the rest of the belt portions such that the free end of the one of said belt portions is distinct and can be readily distinguished from the free end of the other of said belt portions and the ends are distinct and can be readily distinguished from the rest of the belt portions by a user with weak eyesight or in bad light conditions when applying the article.

2. The absorbent article according to claim 1, wherein a geometric difference exists between the free ends of the belt portions to further enable the user to readily distinguish therebetween.

3. The absorbent article according to claim 1, wherein the free end of the one of said belt portions including the fastener is more narrow than the free end of the other of the belt portions to further enable the user to readily distinguish therebetween.

4. The absorbent article according to claim 1, wherein the article is a diaper or an incontinence guard.

* * * * *